United States Patent
Roundhill et al.

[11] Patent Number: 5,993,392
[45] Date of Patent: Nov. 30, 1999

[54] VARIABLE COMPRESSION OF ULTRASONIC IMAGE DATA WITH DEPTH AND LATERAL SCAN DIMENSIONS

[75] Inventors: David N. Roundhill, Bothell; David W. Rust, Seattle, both of Wash.

[73] Assignee: ATL Ultrasound, Inc., Bothell, Wash.

[21] Appl. No.: 08/955,819

[22] Filed: Oct. 22, 1997

Related U.S. Application Data

[60] Provisional application No. 60/030,363, Nov. 5, 1996.

[51] Int. Cl.⁶ ........................................................ A61B 8/00
[52] U.S. Cl. ............................................ 600/447; 600/443
[58] Field of Search ..................................... 600/447, 443, 600/437, 438; 128/916

[56] References Cited

U.S. PATENT DOCUMENTS

| | | | |
|---|---|---|---|
| 4,356,731 | 11/1982 | Mahony . | |
| 4,454,884 | 6/1984 | Seader . | |
| 4,475,400 | 10/1984 | Flax . | |
| 4,537,199 | 8/1985 | Muranaka . | |
| 5,301,674 | 4/1994 | Erikson et al. | 600/447 |
| 5,322,068 | 6/1994 | Thiele et al. | 600/447 |
| 5,438,994 | 8/1995 | Starosta et al. | 600/447 |
| 5,515,852 | 5/1996 | Karp et al. | 128/660.07 |
| 5,543,831 | 8/1996 | Tsuji et al. | 348/65 |
| 5,638,821 | 6/1997 | Nakamura et al. | 600/447 |
| 5,685,308 | 11/1997 | Wright et al. | 600/443 |

FOREIGN PATENT DOCUMENTS

| | | |
|---|---|---|
| 0 484 646 A1 | 5/1992 | European Pat. Off. . |
| 0 539 697 A1 | 5/1993 | European Pat. Off. . |

*Primary Examiner*—Francis J. Jaworski
*Assistant Examiner*—Maulin Patel
*Attorney, Agent, or Firm*—W. Brinton Yorks, Jr.

[57] ABSTRACT

An ultrasonic diagnostic imaging system processes echo information signals by means of a dynamic range map for displayed signals which is varied automatically throughout the image to control the displayed dynamic range and noise rejection level in regions of the image. In a preferred embodiment the displayed dynamic range and noise rejection level varied with both the range (depth) and lateral (scanline to scanline) dimensions of an ultrasonic image.

29 Claims, 6 Drawing Sheets

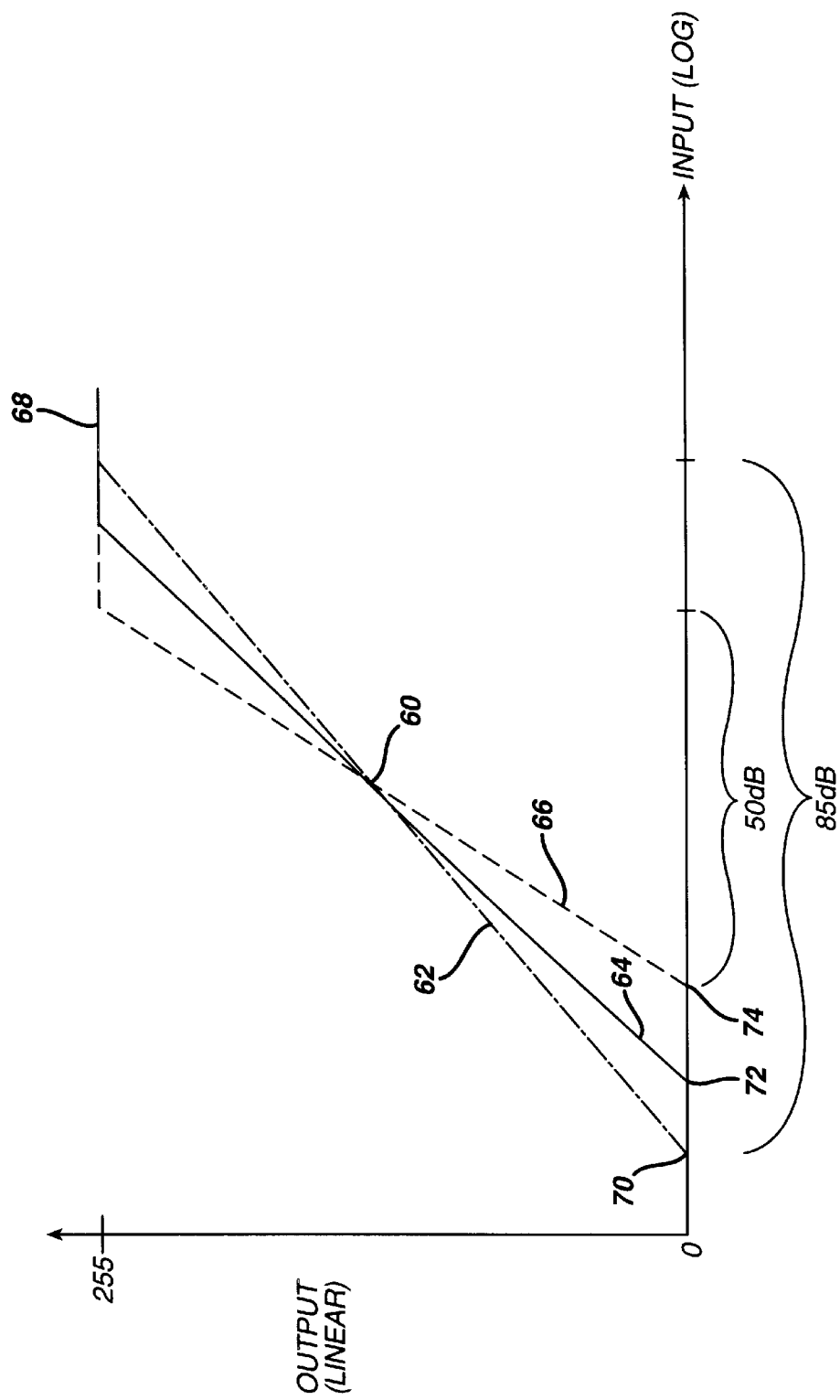

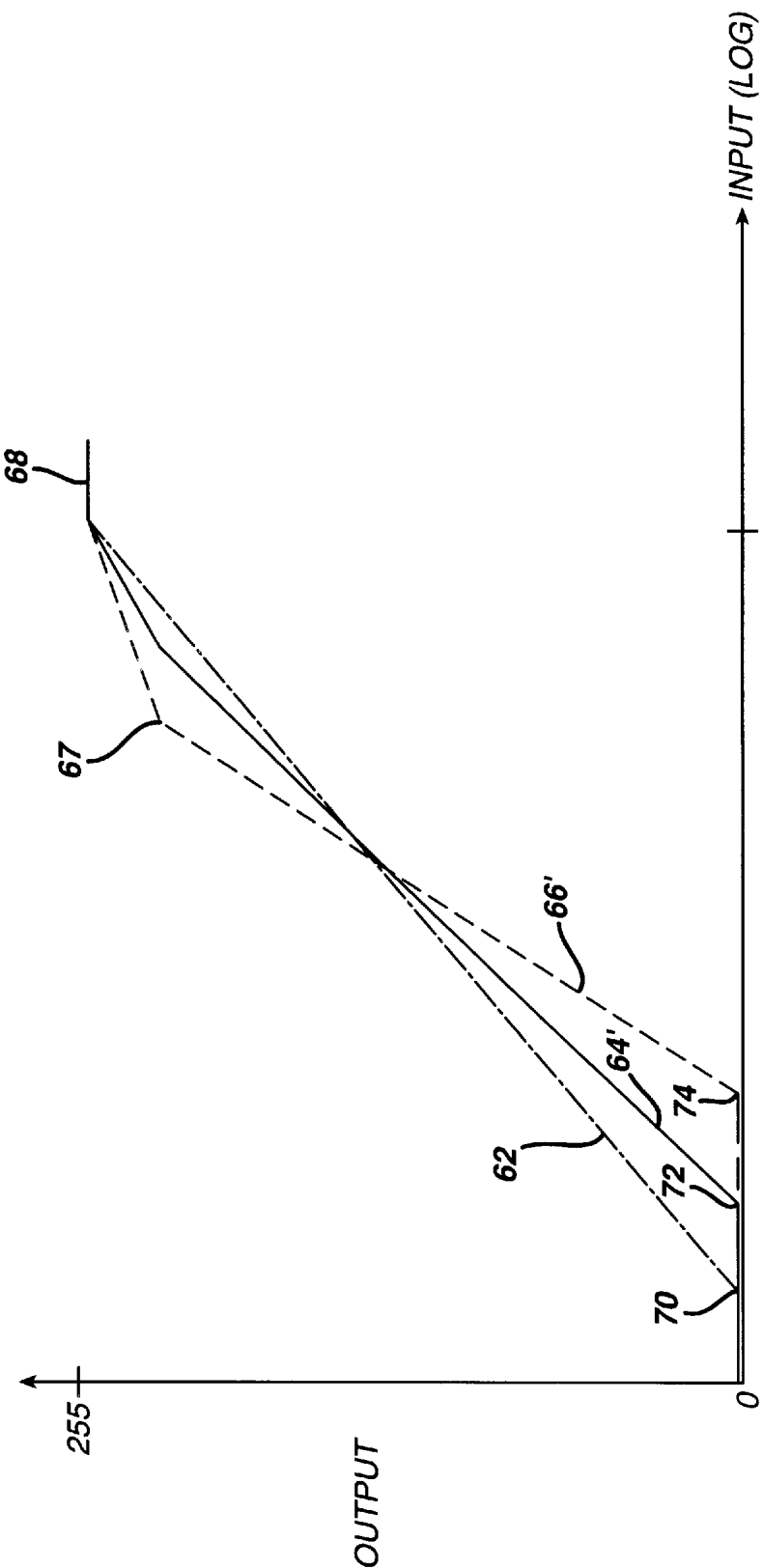

VARIABLE COMPRESSION OF ULTRASONIC IMAGE DATA WITH DEPTH AND LATERAL SCAN DIMENSIONS

This application claims the benefit of U.S. Provisional Application Ser. No. 60/030,363, filed Nov. 5, 1996.

This invention relates to the acquisition and display of medical ultrasonic image data and, in particular, to variation of the dynamic range of such image data as a function of scanning depth and lateral dimension.

When ultrasonic echoes are received from an image field of the body for display, the valid data of the received signal can be quantified in terms of its signal dynamic range of possible values above a noise level. Generally the quantified measure is decibels, where for instance a 60 dB signal is taken to mean that echoes within a range of 60 dB down from a maximum level can be reliably received, and below that low level only noise can be discerned. The common processing response of an ultrasound system to this characteristic is to use signals which fall within the 60 dB range, and discard signals below that range. Thus, valid ultrasonic echoes within the 60 dB range would be displayed, and signals below the noise level of 60 dB down would be clipped off and ignored.

As the technology of ultrasonic receivers has improved, the signal dynamic range over which echoes can be reliably sensed has increased. Ultrasound receivers such as that used by the HDI® 5000 system manufactured by the assignee of the present application are able to discern valid echo signals over a signal dynamic range of 150 dB for instance. However, the signal dynamic ranges of these systems, as well as those of lesser sensitivity, are well beyond the display capability of today's display monitors. Consequently it is conventional to compress the signal dynamic range of the received echoes to a lesser dynamic range for display, usually by a logarithmic compression which more greatly intensifies low level signals relative to stronger signals. The $2^{16}$ possible levels of a sixteen bit received echo signal can be compressed or mapped to $2^8$ logarithmically corresponding levels of a display signal, for instance. Log compression is usually performed toward the end of the ultrasound signal processing sequence after various naturally occurring and systemically induced effects have been eliminated, such as depth dependent attenuation (which is compensated by TGC amplification) and dynamic aperture variation (which is compensated by a normalizing gain or attenuation.)

In the conventional ultrasound system a log compression range is chosen for the imaging procedure which will apply a uniform noise threshold to the imaged region, such as 60 dB in the above example. However, an ultrasonic image field does not exhibit a uniform noise level, due in part to characteristics such as the above mentioned natural and systemic effects and the manner in which they are compensated. The available signal dynamic range at any point in an ultrasound image is a function of several parameters. These include the number of channels used during receive beamforming, the attenuation that the ultrasound beam has undergone and the beam profile as a function of depth. Consequently it would be desirable to produce a display signal which utilizes the full signal dynamic range of valid signals and eliminates noise level signals accurately at every point in the image field.

In accordance with the principles of the present invention, the displayed dynamic range and noise rejection level for displayed signals may be varied automatically throughout the image to control the dynamic range and noise thresholding over the dimensions. In a preferred embodiment the displayed dynamic range and noise rejection level are varied with both the range (depth) and lateral (scanline to scanline) dimensions of an ultrasonic image.

In the drawings:

FIG. 8 illustrates a number of compression maps of one embodiment of the present invention; and FIG. 9 illustrates a number of compression maps of a second embodiment of the present invention.

As used herein the term compression map or compression mapping refers to the application of dynamic range compression and a rejection level to received signals. The term signal dynamic range is representative of the signal to noise ratio, commonly represented as 20 log(maximum signal level/noise level) dB. The noise level is the level at which the desired signal is overwhelmed by undesired signals.

Figure 1:
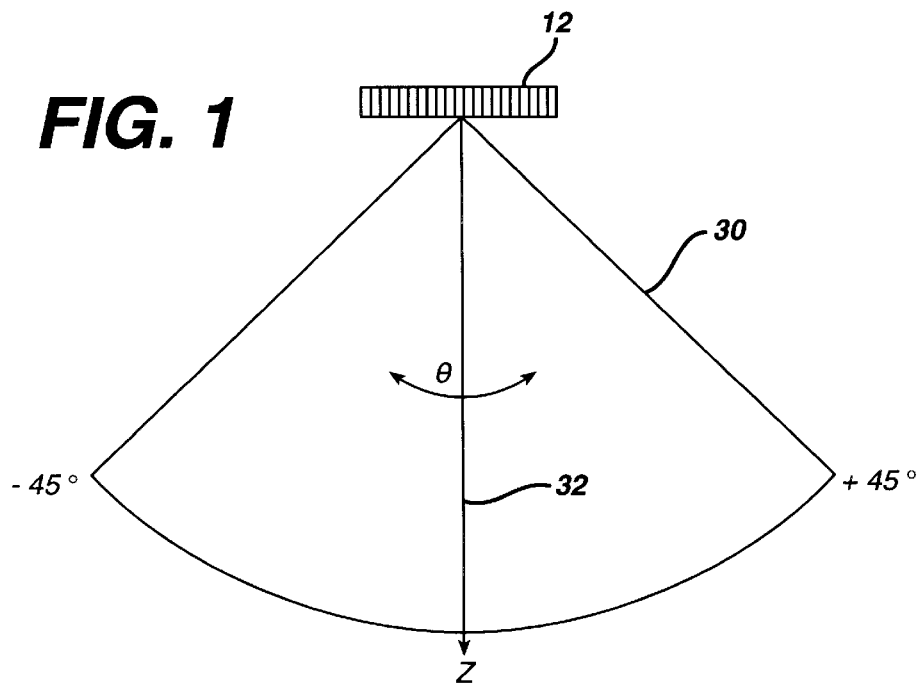
FIG. 1 illustrates a sector image field.

Referring first to FIG. 1, a sector image field 30 is diagrammatically shown emanating from an array transducer 12. In order to scan the sector image field the array transducer transmits and receives ultrasonic energy along scanlines such as scanline 32 at different angles θ relative to the plane of the face of the transducer. Each scanline extends radially into the image field, and echoes are returned from different depths z of the image field along the scanline.

Figure 2:
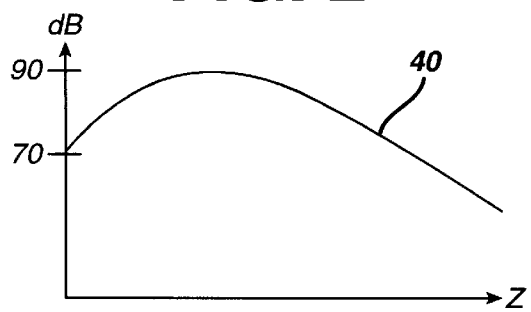
FIG. 2 illustrates an exemplary variation of the signal dynamic range of an ultrasonic image with depth.

A number of different factors can affect the noise level of echo signals returning from along the scanline. One of these factors is variation in the transducer aperture. It is conventional to increase the active aperture of the transducer array as echoes are received from increasing depths, starting from a relatively small number of elements as echoes are received from shallow depths and increasing to a large number of elements as echoes are received from the greater depths z. Another factor is depth dependent attenuation. Echoes which are received from greater depths will be of lower amplitudes and a lesser signal to noise ratio than echoes received from shallower depths z. A composite curve 40 of the influences of these factors is shown in FIG. 2. The curve 40 shows the signal dynamic range initially increasing from 70 dB to 90 dB as the aperture rapidly expands in the near field. The curve peaks at a 90 dB level and then declines as echoes experience depth-dependent attenuation as they are received from greater and greater depths with the same aperture.

Figure 3:
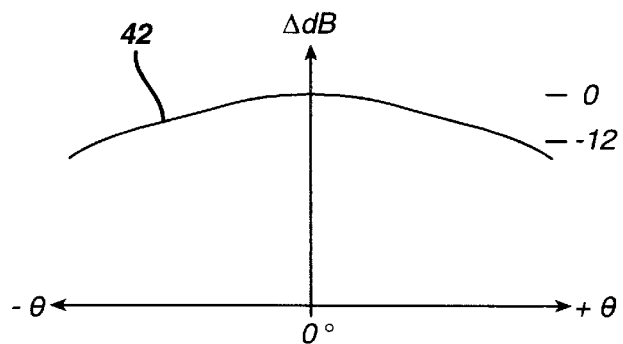
FIG. 3 illustrates an exemplary variation of the signal dynamic range of an ultrasonic image with lateral position.

While the depth dependent effects occur as shown in FIG. 2, other effects occur as a function of the lateral locations of the different scanlines. For a sector scanned image field 30 the scanline 32 in the center of the field is seen to be oriented at right angles to the face of the transducer, allowing a maximal amount of echo energy to be received by the transducer. As echoes are received from along scanlines at increasing angles to normal, in this example up to ±45°, the angle of incidence of the ultrasonic wave and the transducer array declines such that a decreasing amount of echo energy is received for the more lateral scanlines. This declining amount of echo energy with scanline inclination is depicted by curve 42 in FIG. 3, shown as a differential decline ΔdB for a constant depth z across the image field. Thus, the signal dynamic range at any point in the image field 30 is a function of the combined effects of spatially dependent curves such as 40 and 42 at every point in the field.

Figure 4:
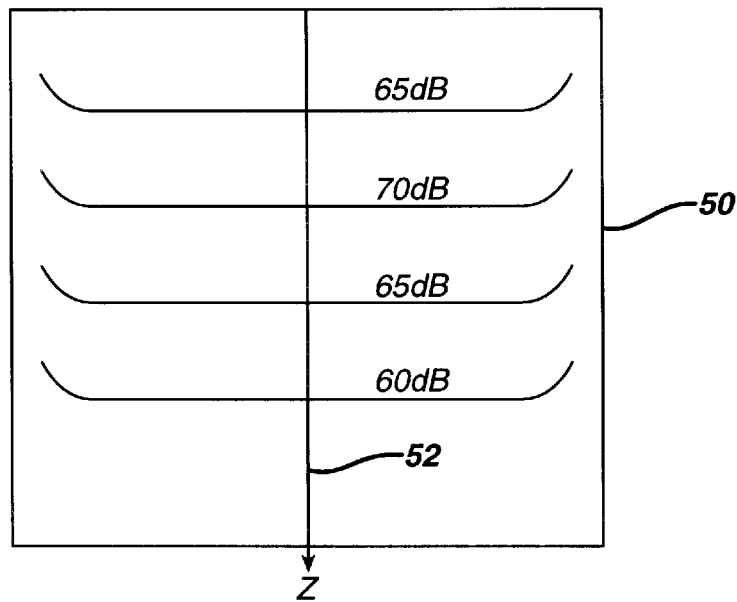
FIG. 4 illustrates boundaries of constant signal dynamic range in a linearly scanned ultrasonic image.

These effects will be different depending upon whether the image field has been scanned as a sector or linearly. FIG. 4, for instance, depicts lines of constant signal dynamic range across a linearly scanned image field 50. In linear scanning, a sequence of parallel scanlines is transmitted and echoes received from the retilinear pattern of scanlines such as central scanline 52. The signal dynamic range in the depth (z) dimension will follow the curve 40 of FIG. 2 as the aperture expands and depth dependent attenuation occurs, just as in the case of the sector scan. This is shown by the dynamic range numbers on the constant signal dynamic range lines, which commence at 65 dB, increase to 70 dB, and then decline to 65 and 60 dB with depth dependent attenuation. However, since each scanline is transmitted and received normal to the face of the transducer, that is, there is no change in the angle of the scanlines relative to the transducer, the lateral variation in the signal dynamic range will not follow curve 42 of FIG. 3. Rather, the lateral signal dynamic range variation is substantially constant across most of the image field 50 as shown by the straight line segments of the lines. The noise level does come up at the lateral sides of the image field 50 as shown by the curved ends of the lines. This is due to the aperture being limited by the lack of further transducer elements as the lateral ends of the array are reached during transmission and reception of the most lateral scanlines.

Figure 5:
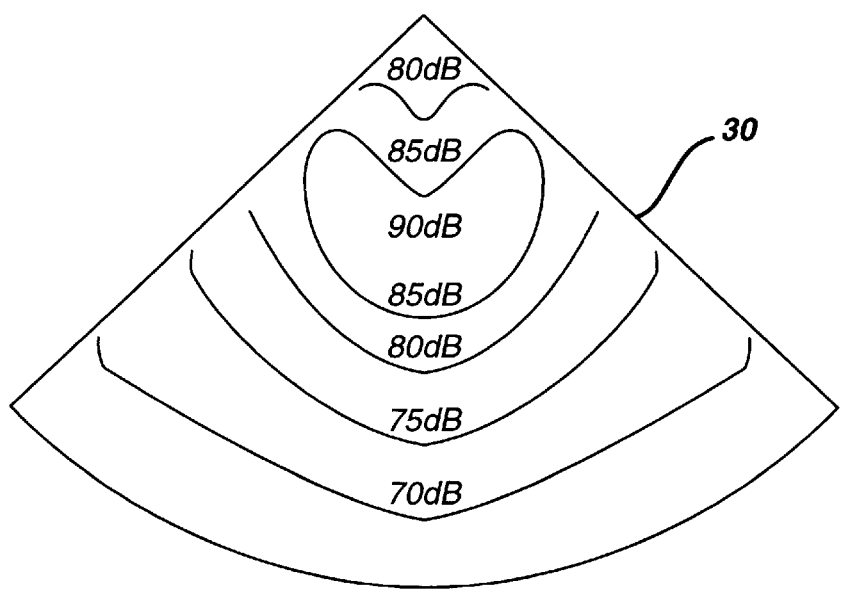
FIG. 5 illustrates boundaries of constant signal dynamic range in a radially scanned ultrasonic image.

In the case of a sector scanned image field 30, the lines of constant signal dynamic range appear as shown in FIG. 5 as a result of the effects depicted by curves 40 and 42. In this illustration the signal dynamic range is seen to be greatest at the point indicated by 90 dB. The signal dynamic range increases to this level at this distance from the transducer, then decreases again with depth, and is seen to decrease with angular scanline displacement from the center of the image field, as the lines of constant signal dynamic range show.

Figure 6:
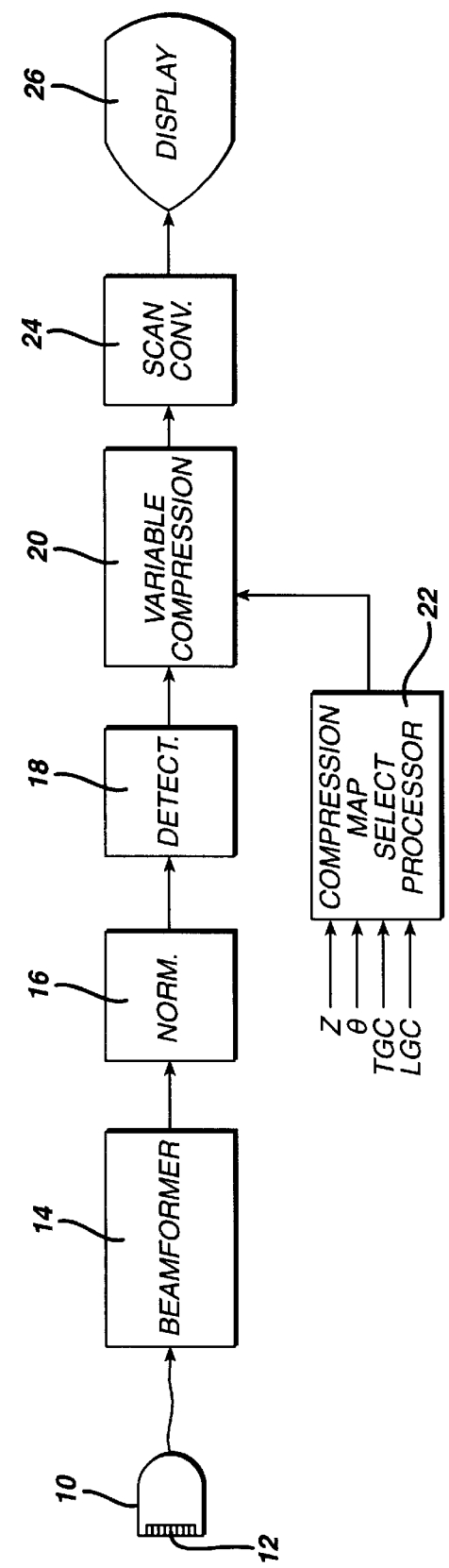
FIG. 6 illustrates in block diagram form an ultrasonic diagnostic imaging system constructed in accordance with the principles of the present invention.

An ultrasonic imaging system which responds to these characteristics is shown in block diagram form in FIG. 6. A scanhead 10 containing the transducer array 12 is coupled to a beamformer 14, which delays and combines signals from the individual transducer elements of the array to form coherent echo signals along each received scanline. The beamformed echo signals are then normalized for the effects of aperture variation by a normalization circuit 16. The normalization circuit applies a gain or attenuation factor to the echo signal to eliminate expanding aperture effects as described more fully in U.S. patent application Ser. No. 08/893,426. With the echo signals equalized for aperture variation, the echo signals are detected by a detection circuit 18 and then mapped in accordance with the principles of the present invention by a variable compression circuit 20. In a preferred embodiment the compression imposed is logarithmic compression whereby the signal dynamic range of the echo signals is mapped to a logarithmic range more suitable for display. The compression and resultant displayed dynamic range and noise threshold imposed is made variable by a compression map select processor 22. The processor 22 selects an appropriate compression map or constants for a processing algorithm in accordance with spatially dependent variables. Four such variables are shown in FIG. 6, including the depth or range z of the echo signals, the angle or lateral position θ of the scanline being processed, a time gain compensation (TGC) curve, or a lateral gain compensation (LGC) curve. Any one of these or other variables may be employed to cause the displayed dynamic range and noise threshold of the echo signals to have a spatial variability. The remapped echo signals are then arranged in the desired image format by a scan converter 24 and displayed on a display 26.

Figure 7:
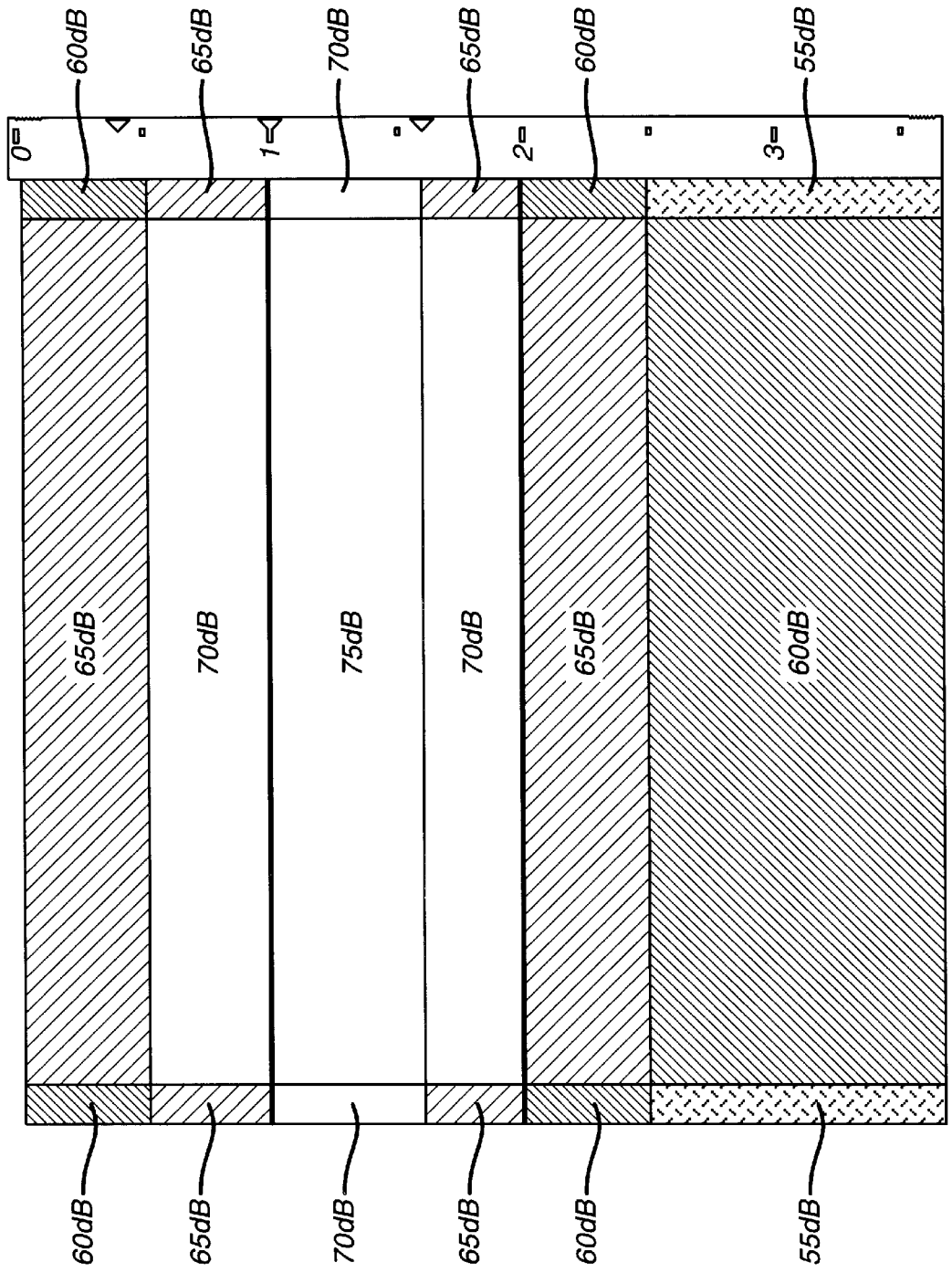
FIG. 7 illustrates a compression map distribution for a linearly scanned image field which varies both laterally and with depth.

There are several ways in which the variable compression circuit 20 can remap the received echo signals to the desired displayed dynamic range and noise threshold map. One is for the processor 22, in response to its input signals, to select a pre-stored compression map which applies the desired variable compression to the received image data. For example, the processor 22 could store and select one of a plurality of fully populated digital look-up tables. For each compression map the table is of a size defined by the input word width. FIG. 7 illustrates such a table which in this example is quantized to 5 dB increments. This table would be used for a linearly scanned image field 50. In the depth (z) dimension the map is seen to comprise discrete bands of compression maps starting with a 65 dB band, increasing to a 75 dB band, then decreasing to a 60 dB band at maximum depth beyond 2.5 cm. At the lateral extremes of the image field the signal dynamic range declines, hence the use of more restricted compression maps. For instance, the 75 dB compression map is reduced to a 70 dB compression map at each lateral extreme, consistent with the lines of constant signal dynamic range shown in FIG. 4.

Rather than store entire compression maps in lookup table forms, another technique is to calculate an output value as each echo value is received, whereby the output value f(x) is calculated from the received echo value x as a function of coefficients a and b which are spatially dependent and provided by the processor 22. For example, an algorithm which may be used for the calculation is $$f(x)=a(log(x)-b) \qquad [1]$$

A pre-compressed digital echo value x is right-shifted until the most significant "1" bit is located to the left of a decimal point and the rest of the digital word is to the right of the decimal point. This expression is, in decimal notation, a value between 1 and 2, and can be expressed as $$w=1+y \qquad [2]$$

The logarithm of a number between 1 and 2 can be evaluated by a polynomial approximation of the form $$log(1+y)=a_1 y+a_2 y^2+a_3 y^3+a_4 y^4+a_5 y^5+\epsilon(y) \qquad [3]$$

where $a_1-a_n$ are fixed coefficients and $|\epsilon(y)| \leq 1 \times 10^{-5}$. Greater precision may be obtained by higher order polynomials, as desired. The log(w) term thus obtained is then used to compute log(x) using the expression $$log(x)=mlog(2)+log(w) \qquad [4]$$

where m is the number of right-shift operations used above to move the echo value x into the range of 1 to 2. The log(x) term of equation [4] is then used in equation [1] together with values of a and b chosen by the processor 22 to find f(x). Each different spatial location in the image field can have its own unique pair of a,b values, or the values can be updated periodically for the desired degree of change from one compression map to the next.

Typical compression maps which can be expressed by a,b notation are shown in FIG. 8. Three compression maps 62,64,66 for a large display dynamic range, moderate display dynamic range, and reduced display dynamic range are shown in the drawing. In this example compression map 62 is seen to have a display dynamic range of 85 dB and compression map 66 is seen to have a display dynamic range of 50 dB, with compression map 64 having an intermediate range. Each compression map extends from a different rejection level 70,72,74, below which noise is eliminated, to a saturation level 68. The compression maps in this example all have different slopes and all intersect at a common point 60. The common point may be centrally located as shown in this example, or anywhere else along the ranges, including at the noise floor or saturation level. The compression maps are shown as straight lines since the abscissa of input values is represented in log scale, while the ordinate of output values is in a linear scale. There are 256 discrete output values in this example, meaning that the output signals can be expressed as eight-bit words.

Each discrete pair of a,b values determines a unique compression curve, where $$a = \text{Output}_{max}/(log\{\text{Input}_{max}\} - b) \quad [5]$$

and $$b = log(\text{Input}_{max}/10^{(DynamicRange/20)}) \quad [6]$$

where $\text{Output}_{max}$ is the maximum compressed output value, $\text{Input}_{max}$ is the point at which the compression map intersects the saturation level 68, and DynamicRange is the display dynamic range in dB. Thus, as echoes are received along a scanline from increasing depths of field, a and b change at a desired rate so that the display dynamic range first begins to increase then decreases with aperture variation and depth dependent attenuation. Correspondingly, the rejection level declines, then increases with aperture variation and depth dependent attenuation. Such change can be driven by a TGC or depth or time function. And as scanlines are received at increasing inclination relative to the transducer plane or toward the sides of a linearly scanned image field, a and b are changed in response to an angle θ or LGC function to gradually reduce the display dynamic range and increase the rejection level for more lateral scanlines. Rather than maintaining a constant rejection level across the entire image field, the rejection level is constantly tailored to the actual noise level at each point or region of the image field.

FIG. 9 illustrates a variation of the compression maps of FIG. 8 in which the compression maps are given an inflection point so as to converge at the saturation level 68 at a common input signal level. As explained in U.S. patent application Ser. No. 08/893,426, this feature reduces the degree of brightness of objects in an ultrasound image which will naturally appear at full brightness, a condition which can limit the ability to discern neighboring structure exhibiting less brightness or definition. The feature does this by limiting the range of saturated output signals (the extent of level 68). Compression map 66', rather than continuing in a straight line (on a log scale) to the saturation level as curve 66 does, exhibits a breakpoint 67 so as to approach and reach saturation level 68 at a higher level of the input signal range. In this example, the point at which the display dynamic range reaches the saturation level does not change with changes in the compression map; all of the compression maps 62, 64', and 66' converge at the saturation level at the same point. Thus, the point at which input signals to the compression circuit 20 produce display signals at the saturation level does not change as different compression maps are used at different points in the image field.

When compression maps with two different slopes are employed, it may be necessary to employ another parameter for the breakpoint 67 in the compression maps, in addition to the a,b parameters. In a constructed embodiment of the present invention, the dynamic range algorithm uses five parameters (a,b,a1,b1, and breakpoint) to dynamically process received echo signals for depth and laterally varying compression maps. The echo value is compared to "breakpoint", and the result of the comparison uses either the a,b or a1,b1 parameter set, thereby determining the proper compression map for each echo value.

As the embodiments of the present invention show, the use of a processor that uses the time gain compensation, depth and line position as inputs allows the automatic selection of compression maps in accordance with variations in the signal dynamic range or other acoustic or systemic characteristics over the width and depth of the image field. The use of look-up tables allows the use of any monotonically increasing function to map the image data. The use of varying compression maps can reduce or eliminate the use of lateral gain amplification to address the effect of off-axis steering and array edge effects.

The principles of the present invention may be applied to ultrasonic image data sets of more than two dimensions to appropriately adjust the dynamic range and noise floor of, for example, three dimensional image data.

What is claimed is:

1. An ultrasonic diagnostic imaging system which produces two dimensional imaged of a region of the body in response to the reception of ultrasonic echoes having differing noise levels, comprising:
   a dynamic range processor, responsive to received ultrasonic echo signals, for varying the displayed dynamic range and noise rejection level of said echo signals over the dimensions of said images; and
   a display, responsive to said dynamic range processor, for displaying said echo signals above said noise rejection level.

2. The ultrasonic diagnostic imaging system of claim 1, wherein said dynamic range processor is responsive to spatial information of said received ultrasonic echo signals.

3. The ultrasonic diagnostic imaging system of claim 2, wherein said dynamic range processor is responsive to the depth from which said echo signals are received for varying the displayed dynamic range and noise rejection level of said echo signals as a function of the depth from which said echo signals were received.

4. The ultrasonic diagnostic imaging system of claim 3, wherein said dynamic range processor is further responsive to the scanline from which said echo signals are received for varying the displayed dynamic range and noise rejection level of said echo signals as a function of the scanline from which said echo signals were received.

5. The ultrasonic diagnostic imaging system of claim 4, wherein said scanlines are arrayed in a parallel orientation.

6. The ultrasonic diagnostic imaging system of claim 4, wherein said scanlines are arrayed in a radial orientation.

7. The ultrasonic diagnostic imaging system of claim 1, wherein said received echo signals have radial and angular coordinates; and wherein said dynamic range processor varies the displayed dynamic range and noise rejection level of said echo signals in response to their radial and angular coordinates.

8. The ultrasonic diagnostic imaging system of claim 1, wherein said received echo signals have radial and lateral coordinates; and wherein said dynamic range processor varies the displayed dynamic range and noise rejection level of said echo signals in response to their radial and lateral coordinates.

9. The ultrasonic diagnostic imaging system of claim 1, wherein said dynamic range processor varies the displayed dynamic range and noise rejection level of said echo signals over a logarithmic range of values.

10. The ultrasonic diagnostic imaging system of claim 9, wherein said dynamic range processor comprises means for scaling said ultrasonic echo signals utilizing a plurality of compression maps.

11. The ultrasonic diagnostic imaging system of claim 9, wherein said dynamic range processor comprises means for scaling said ultrasonic echo signals utilizing an algorithm responsive to echo coordinate information.

12. An ultrasonic diagnostic imaging system which produces an image of a region of the body from an array of ultrasonic echoes exhibiting a varying noise level over the dimensions of an image, comprising:
    a log compression circuit, responsive to received ultrasonic echo signals, for varying the displayed dynamic range and noise rejection level of said echo signals in correspondence with the noise level variation of said image; and
    a display, responsive to said log compression circuit, for displaying said echo signals with varied displayed dynamic range and noise rejection level.

13. The ultrasonic diagnostic imaging system of claim 12, wherein said log compression circuit varies the displayed dynamic range and noise rejection level of said echo signals as a function of the depth from which they are received.

14. The ultrasonic diagnostic imaging system of claim 13, wherein said log compression circuit further varies the displayed dynamic range and noise rejection level of said echo signals as a function of the lateral dimension from which they are received.

15. The ultrasonic diagnostic imaging system of claim 12, wherein said log compression circuit comprises means for mapping said echo signals to displayed dynamic ranges and noise rejection levels which vary as a function of the depth from which they are received.

16. The ultrasonic diagnostic imaging system of claim 15, wherein said log compression circuit further comprises means for mapping said echo signals to displayed dynamic ranges and noise rejection levels which vary as a function of the lateral dimension from which they are received.

17. A method for scaling the display values of ultrasonic echo information received by an ultrasonic diagnostic imaging system, comprising:
    receiving ultrasonic echo information having a noise level which varies over the dimensions of a two dimensional ultrasound image field; and
    mapping said ultrasonic echo information to display dynamic ranges and noise rejection levels which vary with said noise level over said two dimensional ultrasound field.

18. The method of claim 17, wherein said mapping step comprises mapping said ultrasonic echo information to log compressed dynamic ranges.

19. The method of claim 18, wherein said mapping step comprises mapping said ultrasonic echo information to log compressed displayed dynamic ranges exhibiting a plurality of different compression maps.

20. The method of claim 17, wherein said mapping step comprises mapping said ultrasonic echo information to displayed dynamic ranges having minimal values which vary with said noise level and substantially equal maximal values.

21. The method of claim 17, wherein said mapping step comprises mapping said ultrasonic echo information by means of a plurality of predetermined, fully populated compression maps.

22. The method of claim 17, wherein said mapping step comprises mapping said ultrasonic echo information by means of a variable dynamic range conversion algorithm.

23. The method of claim 22, wherein said mapping step comprises mapping said ultrasonic echo information by means of a variable log compression algorithm.

24. A method for mapping the values of ultrasonic echo information received by an ultrasonic diagnostic imaging system, comprising:
    receiving ultrasonic echo signals having values occupying a range of values over the dimensions of a two dimensional ultrasound image field; and
    mapping said ultrasonic echo signal values to a logarithmically compressed range of values which varies over the depth of said image field.

25. The method of claim 24, wherein said logarithmically compressed range of values further varies over the lateral dimension of said image field.

26. A method for mapping the values of ultrasonic echo information received by an ultrasonic diagnostic imaging system, comprising:
    receiving ultrasonic echo signals having values occupying a signal dynamic range; and
    numerically computing display values of a spatially variable compressed dynamic range from said received ultrasonic echo signals as said echo signals are received.

27. The method of claim 26, wherein the step of numerically computing display values utilizes a compression map algorithm.

28. The method of claim 27, wherein the step of numerically computing display values utilizes a plurality of different compression map algorithms.

29. The method of claim 28, wherein the step of numerically computing display values includes selecting a compression map algorithm in accordance with the spatial origin of an ultrasonic echo signal.

* * * * *